US012310855B2

(12) United States Patent
Prevost et al.

(10) Patent No.: US 12,310,855 B2
(45) Date of Patent: May 27, 2025

(54) END CAP AND BONE SCREW FOR USE THEREWITH

(71) Applicant: WARSAW ORTHOPEDIC, INC., Warsaw, IN (US)

(72) Inventors: Julien J. Prevost, Memphis, TN (US); Aubrey R. Mills, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/939,678

(22) Filed: Sep. 7, 2022

(65) Prior Publication Data

US 2023/0075024 A1  Mar. 9, 2023

Related U.S. Application Data

(60) Provisional application No. 63/242,358, filed on Sep. 9, 2021.

(51) Int. Cl.
  *A61F 2/30*  (2006.01)
  *A61F 2/44*  (2006.01)

(52) U.S. Cl.
  CPC ...... *A61F 2/30734* (2013.01); *A61F 2/30749* (2013.01); *A61F 2/44* (2013.01);
  (Continued)

(58) Field of Classification Search
  CPC .... A61F 2/30734; A61F 2/30749; A61F 2/44; A61F 2002/305; A61F 2002/30505; A61F 2002/30774; A61F 2002/30892
  See application file for complete search history.

(56) References Cited

U.S. PATENT DOCUMENTS 6,808,538 B2  10/2004  Paponneau
7,544,208 B1   6/2009  Mueller et al.
(Continued)

FOREIGN PATENT DOCUMENTS

CN    102421391   4/2012
WO    2008065450  6/2008
(Continued)

OTHER PUBLICATIONS

European Search Report and Written Opinion dated Feb. 10, 2023 in EP22194571.0.

*Primary Examiner* — Nicholas J Plionis

(57) ABSTRACT

An end cap and a bone screw for use therewith are provided. One or more of the end caps can be used with a spinal implant used to replace portions of a vertebral body after a corpectomy thereof. The end cap can include a first end and a second end opposite from one another, a first side and a second side opposite from one another, and a body portion extending between the first end, the second end, the first side, and the second side. The body portion can include an exterior surface for contacting an endplate of a vertebral body, and an interior cavity formed in the end cap opposite from the exterior surface. The interior cavity can be sized to receive a flange portion of the spinal implant, and can include at least one attachment structure provided in the interior cavity facilitating attachment of the end cap to the flange portion of the spinal implant. One or more of the bone screws can be received through apertures formed in the end cap and into the endplate of the vertebral body. The bone screws can be configured, upon receipt in the apertures in the end caps, to lock in place relative thereto.

20 Claims, 9 Drawing Sheets

(52) U.S. Cl.
CPC .................. *A61F 2002/305* (2013.01); *A61F 2002/30505* (2013.01); *A61F 2002/30774* (2013.01); *A61F 2002/30892* (2013.01)

(56) References Cited

U.S. PATENT DOCUMENTS

| | | | |
|---|---|---|---|
| 7,942,903 B2 | 5/2011 | Moskowitz et al. | |
| 8,137,405 B2 | 3/2012 | Kostuik et al. | |
| 8,202,321 B2 | 6/2012 | Gener | |
| 8,211,178 B2 | 7/2012 | Melkent et al. | |
| 8,372,151 B2 | 2/2013 | Hsu et al. | |
| 8,613,768 B2 | 12/2013 | Biedermann et al. | |
| 8,945,228 B2 | 2/2015 | Popa et al. | |
| 9,301,850 B2* | 4/2016 | McLaughlin | A61F 2/446 |
| 9,333,088 B2 | 5/2016 | Berger et al. | |
| 9,393,128 B2 | 7/2016 | Hansell et al. | |
| 9,724,208 B2* | 8/2017 | Robinson | A61F 2/4455 |
| 9,801,730 B2 | 10/2017 | Howard et al. | |
| 9,974,663 B2 | 5/2018 | Stinchfield et al. | |
| 10,226,352 B2 | 3/2019 | Lorenz et al. | |
| 10,987,229 B2 | 4/2021 | Stinchfield et al. | |
| 2009/0138089 A1 | 5/2009 | Doubler et al. | |
| 2010/0249935 A1 | 9/2010 | Slivka et al. | |
| 2011/0218631 A1* | 9/2011 | Woodburn, Sr. | A61F 2/4611 623/17.16 |
| 2012/0109302 A1* | 5/2012 | Miller | A61F 2/4455 29/446 |
| 2014/0135933 A1 | 5/2014 | Mcclintock et al. | |
| 2014/0207236 A1 | 7/2014 | Prevost et al. | |
| 2015/0142115 A1* | 5/2015 | Richerme | A61F 2/447 623/17.16 |
| 2015/0216670 A1 | 8/2015 | Davenport et al. | |
| 2015/0335445 A1 | 11/2015 | Stinchfield et al. | |
| 2016/0100955 A1 | 4/2016 | Stinchfield et al. | |
| 2016/0175103 A1 | 6/2016 | Howard | |
| 2016/0193057 A1 | 7/2016 | Rhoda | |
| 2017/0360572 A1 | 12/2017 | Bannigan et al. | |
| 2019/0247199 A1* | 8/2019 | Stinchfield | A61F 2/4465 |

FOREIGN PATENT DOCUMENTS

| | | |
|---|---|---|
| WO | 2014/145982 | 9/2014 |
| WO | 2017049268 | 3/2017 |

* cited by examiner

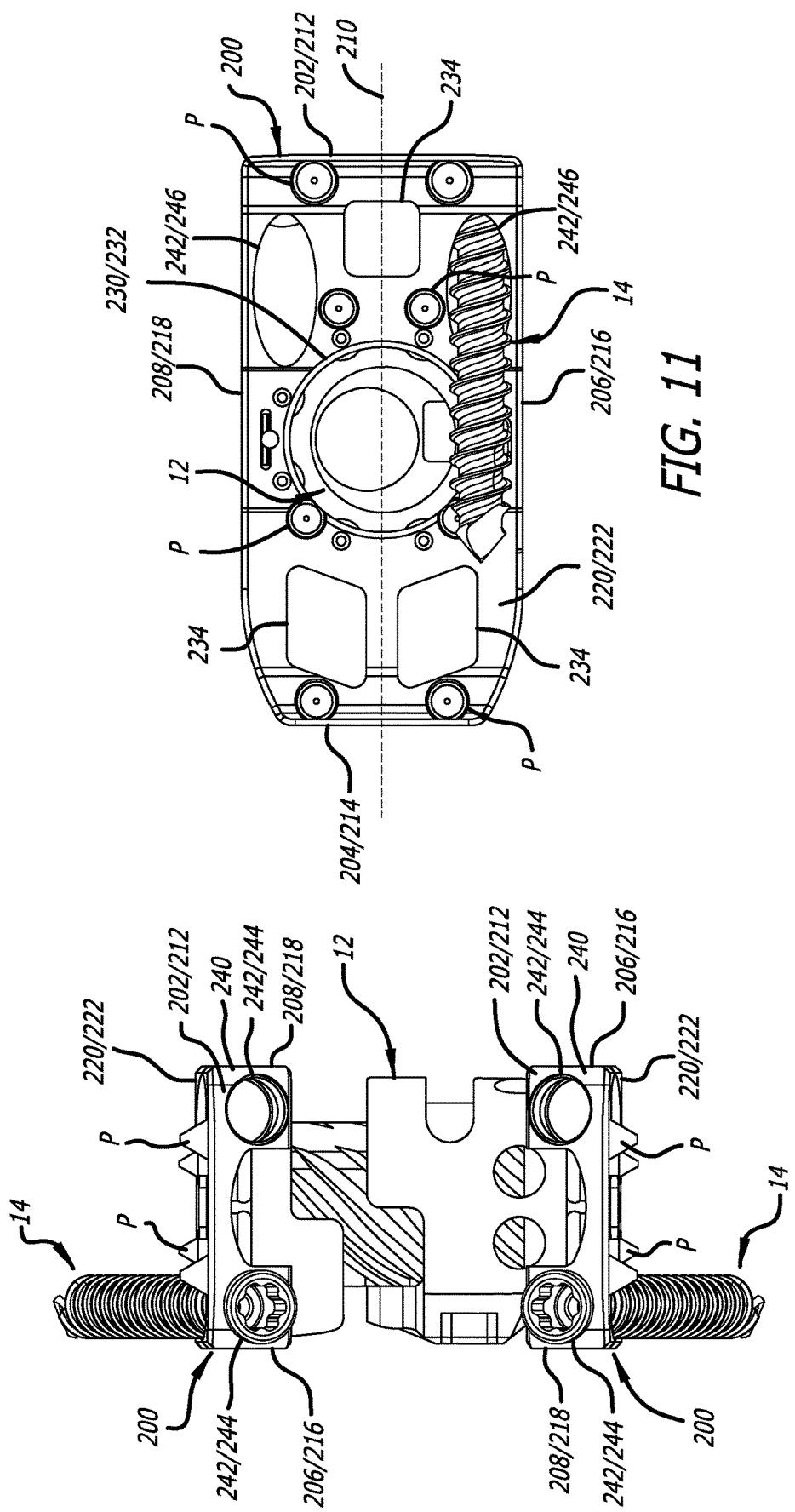

END CAP AND BONE SCREW FOR USE THEREWITH

This application claims the benefit of U.S. Provisional Application No. 63/242,358, filed Sep. 9, 2021, which is incorporated by reference herein.

FIELD

The present technology generally relative to an end cap and a bone screw for use therewith. One or more of the end caps can be used as or with spinal implants to replace a vertebral body or bodies after a corpectomy. A first one of the end caps can be attached to a first end portion and a second one of the end caps can be attached to a second end portion of such a corpectomy implant.

BACKGROUND

Spinal disorders oftentimes requires removal of a vertebral body or bodies from the spine of a patient. An intervertebral space between the remaining vertebral bodies is typically bridged by instrumentation to stabilize the spine. Various spinal implants such as, for example, corpectomy devices, whether unexpandable or expandable, typically have been used as the instrumentation to stabilize the spine. Such corpectomy devices can have end portions for engaging endplates of the vertebral bodies bordering the intervertebral space. However, oftentimes there is a need for flexibility in providing additional height and/or angularity of the ultimate construct for implantation in the intervertebral space. The present invention is directed to one or more end caps that can be attached to a corpectomy device to provide such additional height to facilitate bridging of the intervertebral space, and/or to provide angular surfaces for engaging the endplates of the vertebral bodies to, for example, facilitate lordotic and/or kyphotic restoration. The increased height, the angular surfaces, and/or other anti-migration features of the end caps can increase the stability and anti-migration strength of the resulting combination with the corpectomy device.

SUMMARY

The techniques of this disclosure generally relate to an end cap and a bone screw for use therewith. As discussed below, one or more the end caps can be used as or with spinal implants to replace a vertebral body or bodies after a corpectomy. To illustrate, a first one of the end caps can be attached to a first end portion and a second one of the end caps can be attached to a second end portion of such a corpectomy device. When used in combination with such the corpectomy device, the end caps can, for example, be used to increase the height, angularity, stability, and anti-migration strength of the resulting combination.

In one aspect, the present disclosure provides an end cap for use with a spinal implant used to replace portions of a vertebral body after a corpectomy thereof, the end cap including a first end and a second end opposite from one another, a first side and a second side opposite from one another, and a mid-longitudinal axis extending through the first end and the second end; a body portion extending between the first end, the second end, the first side, and the second side, the body portion including an exterior surface for contacting an end plate of a vertebral body; and an interior cavity formed in the end cap opposite from the exterior surface, the interior cavity being defined by an interior surface of the body portion and various side surfaces defining a perimeter of the interior cavity; where the interior cavity is sized to receive a flange portion of the spinal implant, and includes at least one attachment structure provided in the interior cavity facilitating attachment of the end cap to the flange portion of the spinal implant.

In another aspect, the present disclosure provides an end cap for use with a spinal implant used to replace portions of a vertebral body after a corpectomy thereof, the end cap including a first end and a second end opposite from one another, a first side and a second side opposite from one another, and a mid-longitudinal axis extending through the first end and the second end; a body portion extending between the first end, the second end, the first side, and the second side, the body portion including an exterior surface for contacting an end plate of a vertebral body; an interior cavity formed in the end cap opposite from the exterior surface, the interior cavity being defined by an interior surface of the body portion and various side surfaces defining a perimeter of the interior cavity; and a rim surface surrounding at least portions of the interior cavity; where the interior cavity is sized to receive a flange portion of the spinal implant, and includes at least one attachment structure provided in the interior cavity facilitating attachment of the end cap to the flange portion of the spinal implant; and where at least portions of the exterior surface reside in a first plane, and at least portions of the rim surface reside in a second plane, the first plane and the second plane being one of parallel to one another, substantially parallel to one another, and oriented at an acute angle to one another.

In yet another aspect, the present disclosure provides an end cap for use with a spinal implant used to replace portions of a vertebral body after a corpectomy thereof, the end cap including a first end and a second end opposite from one another, a first side and a second side opposite from one another, and a mid-longitudinal axis extending through the first end and the second end; a body portion extending between the first end, the second end, the first side, and the second side, the body portion including an exterior surface for contacting an end plate of a vertebral body; and an interior cavity formed in the end cap opposite from the exterior surface; where the interior cavity is sized to receive a flange portion of the spinal implant, and includes at least one attachment structure for facilitating attachment of the end cap to the flange portion of the spinal implant; and where the first end and the second end are spaced apart from one another a first maximum distance, and the first side and the second end are spaced apart from one another a second maximum distance, the first maximum distance being approximately twice as large as the second maximum distance.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The techniques of this disclosure generally relate to an end cap and a bone screw for use therewith.

FIG. 10 is an end elevation view of the first and second ones of end caps of FIG. 9 attached relative to the spinal implant of FIG. 4 and the first and second ones of the bone screws of the present disclosure inserted through the first and second ones of the end caps, respectively;

FIG. 11 is a top plan view of the first one of end caps of FIG. 9 attached relative to the spinal implant of FIG. 4, and the first one of the bone screws of the present disclosure inserted in the first one of the end caps;

DETAILED DESCRIPTION

Figure 1:
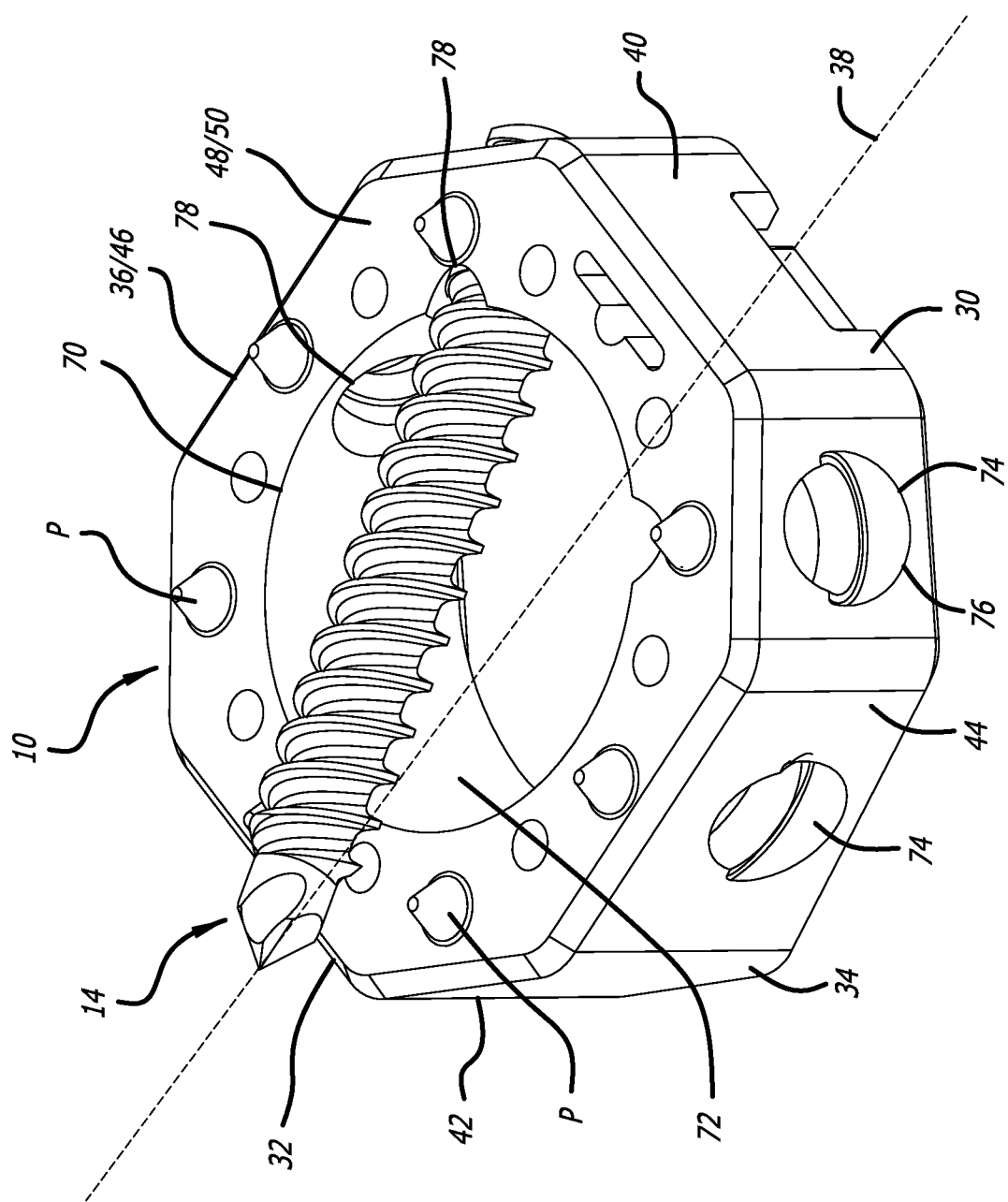
FIG. 1 is a top perspective view of a first embodiment of an end cap of the present disclosure with a bone screw of the present disclosure inserted through a portion of the end cap.
Figure 2:
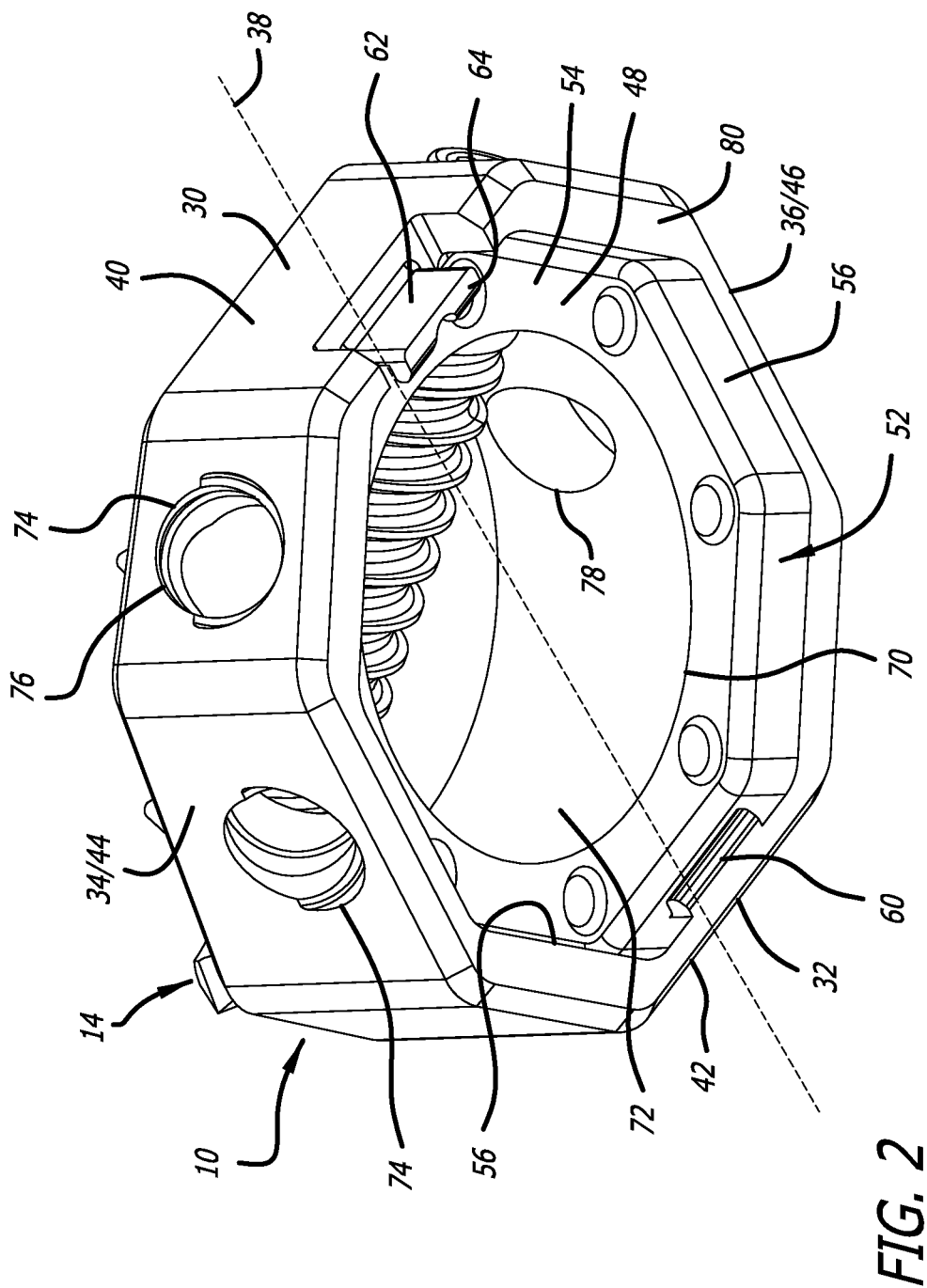
FIG. 2 is a bottom perspective view of the end cap and the bone screw of FIG. 1.
Figure 3:
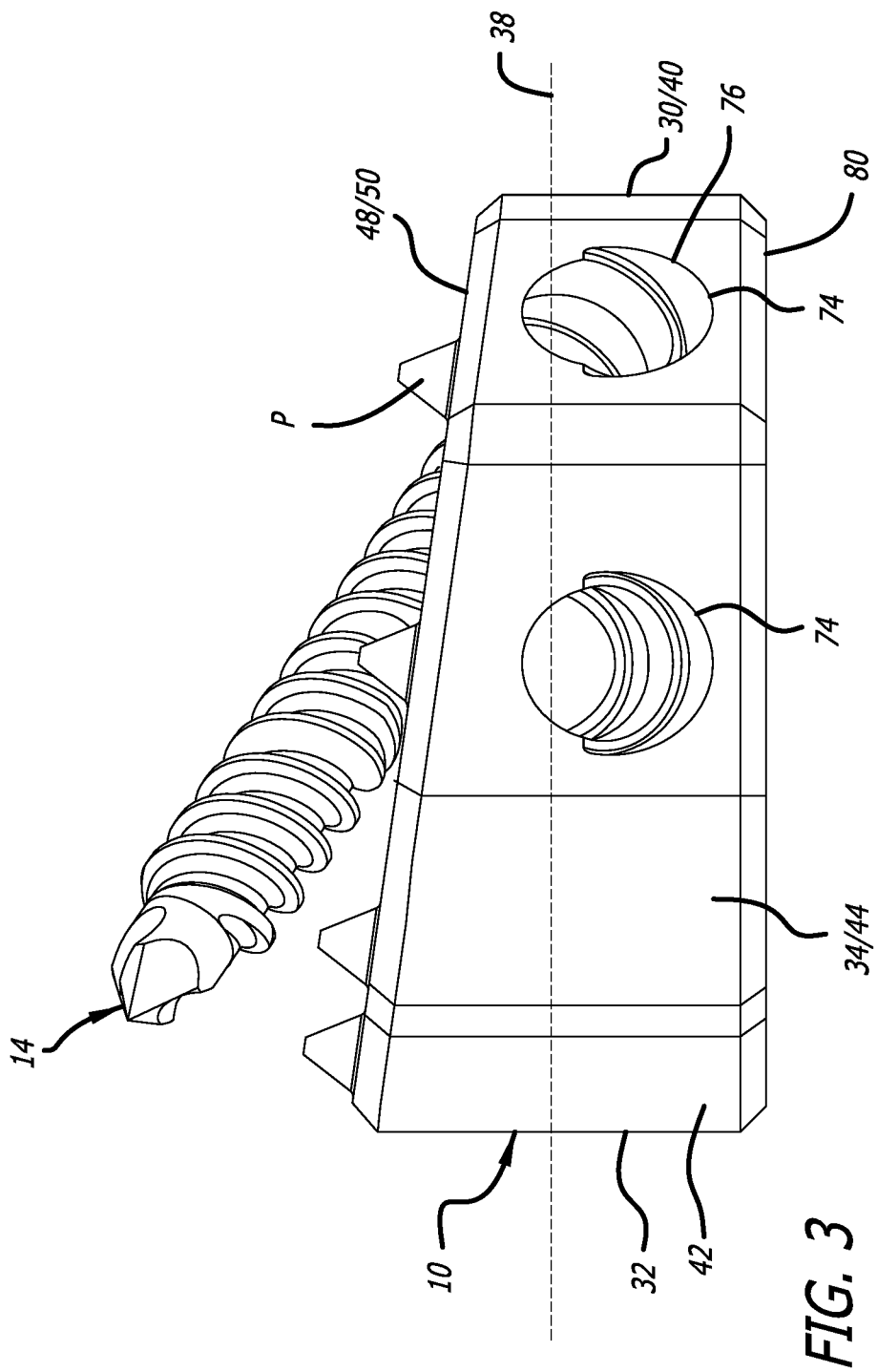
FIG. 3 is a side elevational view of the end cap and the bone screw of FIG. 1.

An end cap according to one embodiment of the present disclosure is generally indicated by the numeral 10 in FIGS. 1-3. One or more of the end caps 10 can be used with spinal implants disclosed, for example, in U.S. Pat. Nos. 9,974,663, 10,624,759, and 10,987,229, which are hereby incorporated by reference. The spinal implants disclosed in the above-referenced patents can be used as vertebral body replacements for replacing a vertebral body after a corpectomy has been performed on that vertebral body. A spinal implant similar to those disclosed in the above-referenced patents is generally indicated by the numeral 12 in FIGS. 4, 5, and 9-11.

One of more of the end caps 10 can be attached to the spinal implant 12 to, for example, increase the height, angularity, stability and anti-migration strength of the resulting combination. To that end, each of the end caps 10, for example, can include one or more anti-migration surface features for engaging endplates of vertebral bodies, can provide one or more apertures for receiving threaded bone screws 14 that are insertable therethrough and into the endplates of the vertebral bodies, and/or can provide angled surfaces for engaging the endplates of the vertebral bodies to facilitate lordotic and/or kyphotic restoration. Additionally, as discussed below, the threaded bone screws 14 can be configured, upon receipt in the apertures in the end caps 10, to lock in place relative thereto.

Figure 4:
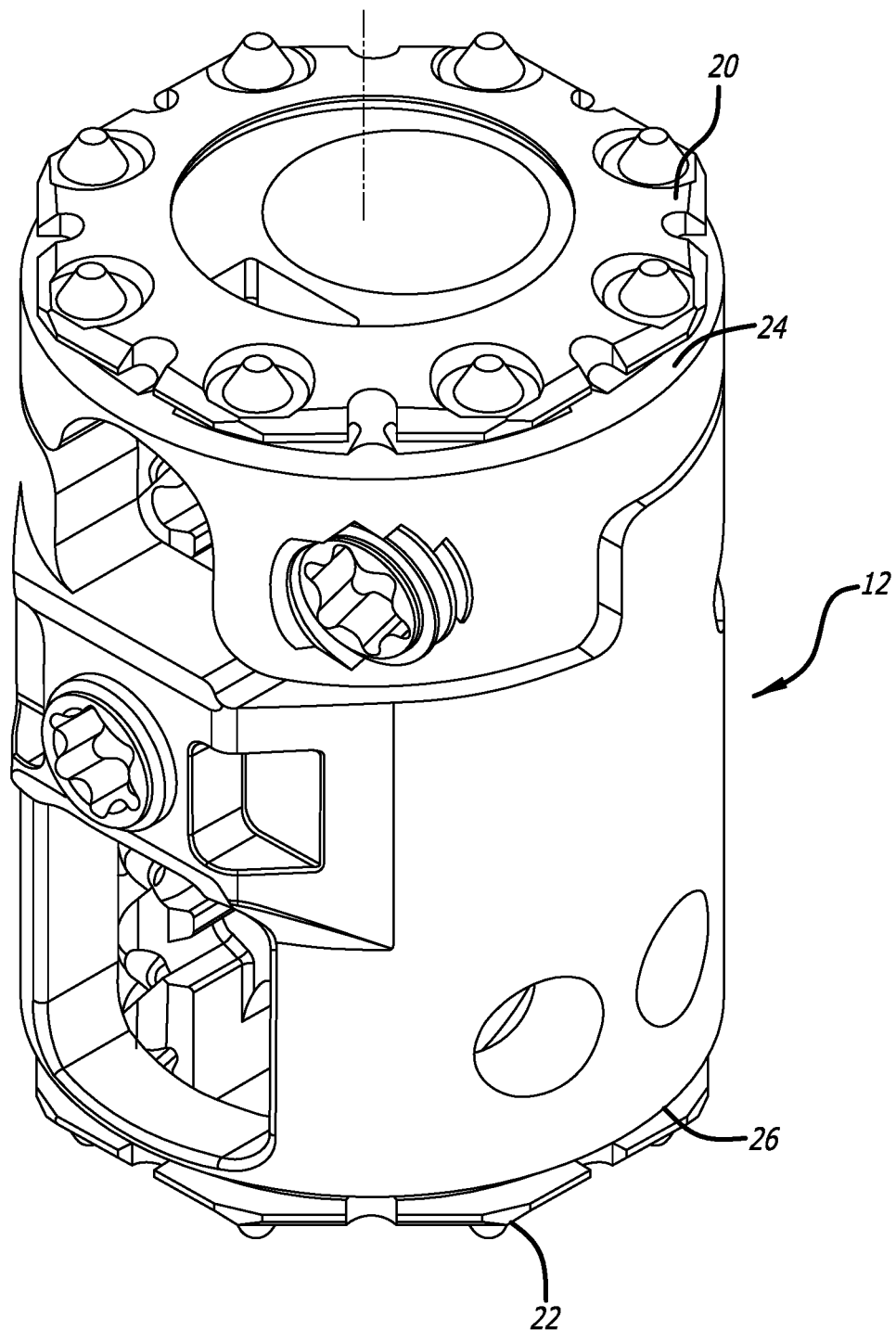
FIG. 4 is a perspective view of a spinal implant with which end caps of the present disclosure can be used.
Figure 5:
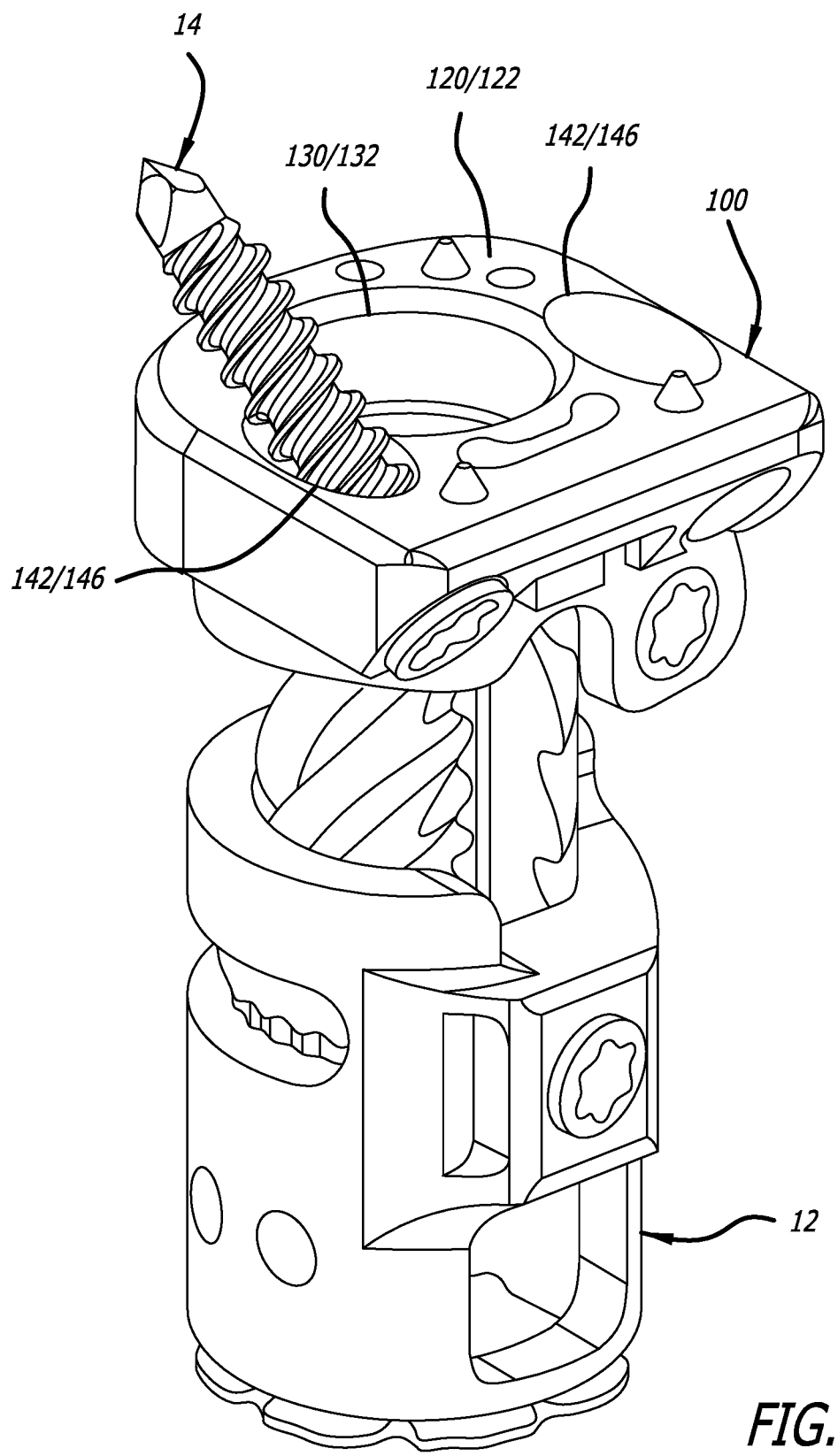
FIG. 5 is a perspective view of a second embodiment of an end cap of the present disclosure with one of the end caps attached relative to the spinal implant of FIG. 4 and the bone screw of the present disclosure inserted through a portion of the end cap.

As depicted in FIG. 4, the spinal implant 12 is expandable, and includes a first flange portion 20 at an upper first end thereof and a second flange portion 22 at a lower second end thereof. The expansion of the spinal implant 12 serves to increase the distance between the first flange portion 20 and the second flange portion 22. Furthermore, a first recess 24 is provided adjacent the first flange portion 20 and a second recess 26 is provided adjacent the second flange portion 22. As discussed below, a first one of the end caps 10 can be attached to the first flange portion 20 and a second one of the end caps 10 can be attached to the second flange portion 22.

As depicted in FIGS. 1-3, the end cap 10 includes a first end 30, a second end 32, a first side 34, a second side 36, and a mid-longitudinal axis 38 extending through the first end 30 and the second end 32. Furthermore, as depicted in FIGS. 1-3, the end cap 10 can include first endwall 40 at and adjacent the first end 30, a second endwall 42 at and adjacent the second end 32, a first sidewall 44 adjacent the first side 34, a second sidewall 46 adjacent the second side 36, and a body portion 48 (FIGS. 1 and 2) extending between the first endwall 40, the second endwall 42, the first sidewall 44, and the second sidewall 46.

An exterior surface 50, as depicted in FIG. 1, can be formed on the body portion 48. The exterior surface can extend between the first end 30, the second end 32, the first side 34, and the second side 36. The exterior surface 50 can be shaped to conform or substantially conform to the endplate of a vertebral body, and/or can include one or more projections P formed thereon for penetrating into the endplate. As such, when engaged to the endplate of the vertebral body, the shape of the exterior surface 50 and the projections P serve as the anti-migration features inhibiting movement of the end cap 10 (and the spinal implant 10 attached thereto) relative to the vertebral body.

As depicted in FIG. 2, an interior cavity 52 can formed on an opposite side of the exterior surface 50, and the interior cavity 52 can be defined at least in part by an interior surface 54 of the body portion 48 opposite the exterior surface 50, and side surfaces 56 defining a perimeter of the interior cavity 52. The perimeter defined by the side surfaces 56 can be sized to correspond to the shapes of the first flange portion 20 and the second flange portion 22 to facilitate receipt of one of the first flange portion 20 and the second flange portion 22 in the interior cavity 52.

To facilitate attachment of the end cap 10 to the first flange portion 20 or the second flange portion 22, the interior cavity 52, as depicted in FIG. 2, can include a lip portion 60 and a flexible detent portion 62 (with a nub 64) provided therein that are used to facilitate attachment of either of the first flange portion 20 and the second flange portion 22 to end cap 10. The lip portion 60 can extend inwardly from one of the side surfaces 56, and the flexible detent portion 62 can extend downwardly from the interior surface 54 across from the lip portion 60.

To attach the end cap 10 to one of the first flange portion 20 and the second flange portion 22 of the spinal implant 12, a first portion of the first flange portion 20 or the second flange portion 22 can be received between the lip portion 60 and the interior surface 54 with a portion of the lip portion being received in a corresponding one of the first recess 24 and the second recess 26. Thereafter, a second portion of the first flange portion 20 or the second flange portion 22 can be pushed past the nub 64 of the flexible detent portion 62, so that the second portion of the first flange portion 20 or the second flange portion 22 is received between the nub 64 and the interior surface 54 with a portion of the nub 64 being received in a corresponding one of the first recess 24 and the second recess 26. By capturing a portion of the first flange portion 20 or the second flange portion 22 between the lip portion 60 and the interior surface 54 and another portion of the first flange portion 20 or the second flange portion 22 between the nub 64 and the interior surface 54, the end cap 10 can be attached to the spinal implant 12.

An aperture 70 with a sidewall 72, as depicted in FIGS. 1 and 2, can be provided in the end cap 10 between the exterior surface 50 and the interior surface 54. The aperture 70 can afford access to the spinal implant 12, and/or to afford bone growth from the endplate of the vertebral body therethrough and into the spinal implant 12. Additionally, as depicted in FIGS. 1-3, bone screw holes 74 can extend through the end cap 10 between first openings 76 formed in the first endwall 40, the second endwall 42, the first sidewall 44, and/or the second sidewall 46, and second openings 78 formed in the sidewall 72 of the aperture 70. The second openings 78 can also be formed all or in part in the exterior surface 50. The locations of the bone screw holes 74 can afford multiple surgical approaches including, for example, posterior, lateral, or postero-lateral approaches.

The bone screws holes 74 can be threaded to engage the threaded bone screws 14 therein. When the end cap 10 is positioned adjacent the endplate of the vertebral body, the threaded bone screws 14 can be inserted through the bone screw holes 74 and into the endplate to prevent migration of the end cap 10 (and the spinal implant 12 attached thereto) relative to the vertebral body.

Additionally, the end cap 10 can be configured to have an angled exterior surface 50 to create a lordotic angle or a kyphotic angle for engaging the endplate of the vertebral body. To illustrate, a rim surface 80, as depicted in FIG. 2, can be formed on the first endwall 40, the second endwall 42, the first sidewall 44, and the second sidewall 46 adjacent the interior cavity 52 and/or around the perimeter thereof. At least portions of the rim surface 80 can reside in a first plane, and at least portions of the exterior surface 50 can reside in a second plane angled with respect to the first plane. The exterior surface 50 can be angled so that the first plane and the second plane are parallel or substantially parallel to one another, or the exterior surface 50 can be angled so that the first plane is oriented at an acute angle with respect to the second plane. The endplate can be configured to provide a desired lordotic angle or kyphotic angle by providing a corresponding acute angle of the first plane relative to the second plane. Instead of or in addition to the desired lordotic angle or kyphotic angle, the exterior surface 50 could also be convex in planes aligned with or transverse to the mid-longitudinal axis 38.

Figure 7:
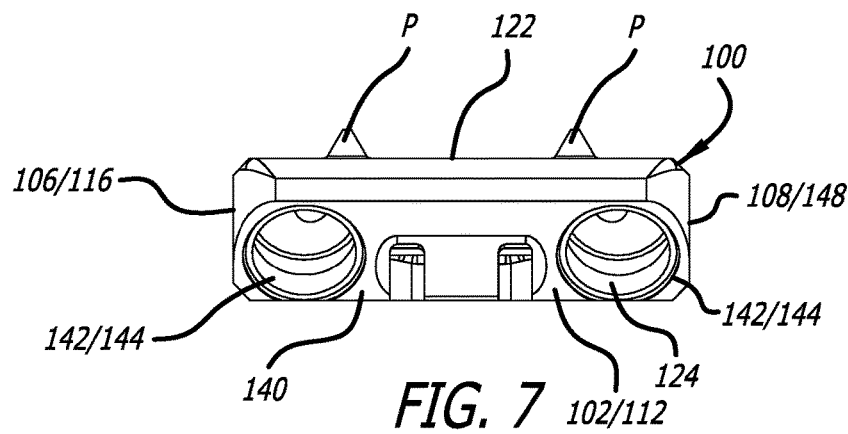
FIG. 7 is an end elevational view of the end cap of FIG. 5.
Figure 8:
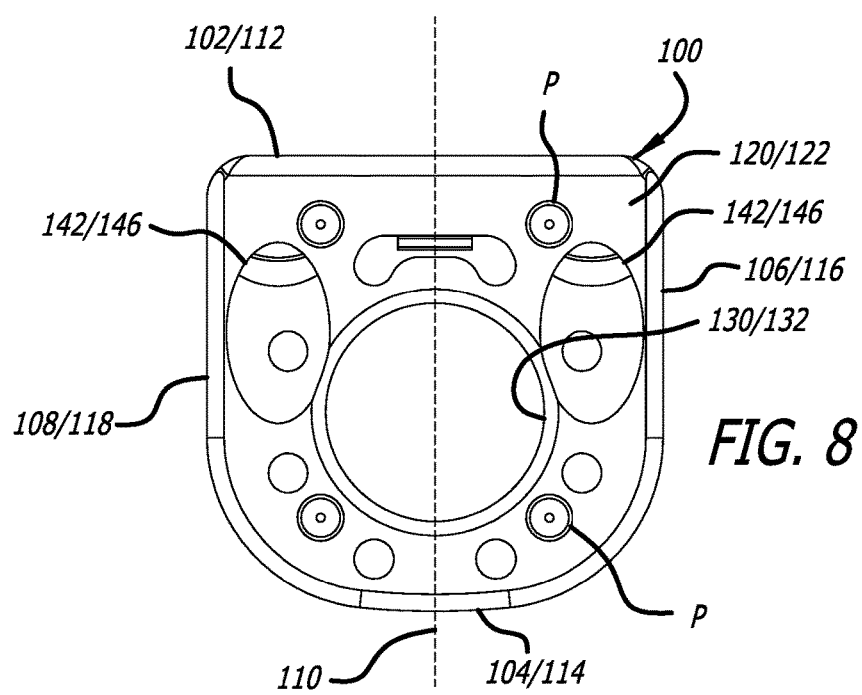
FIG. 8 is a top plan view of the end cap of FIG. 5.
Figure 9:
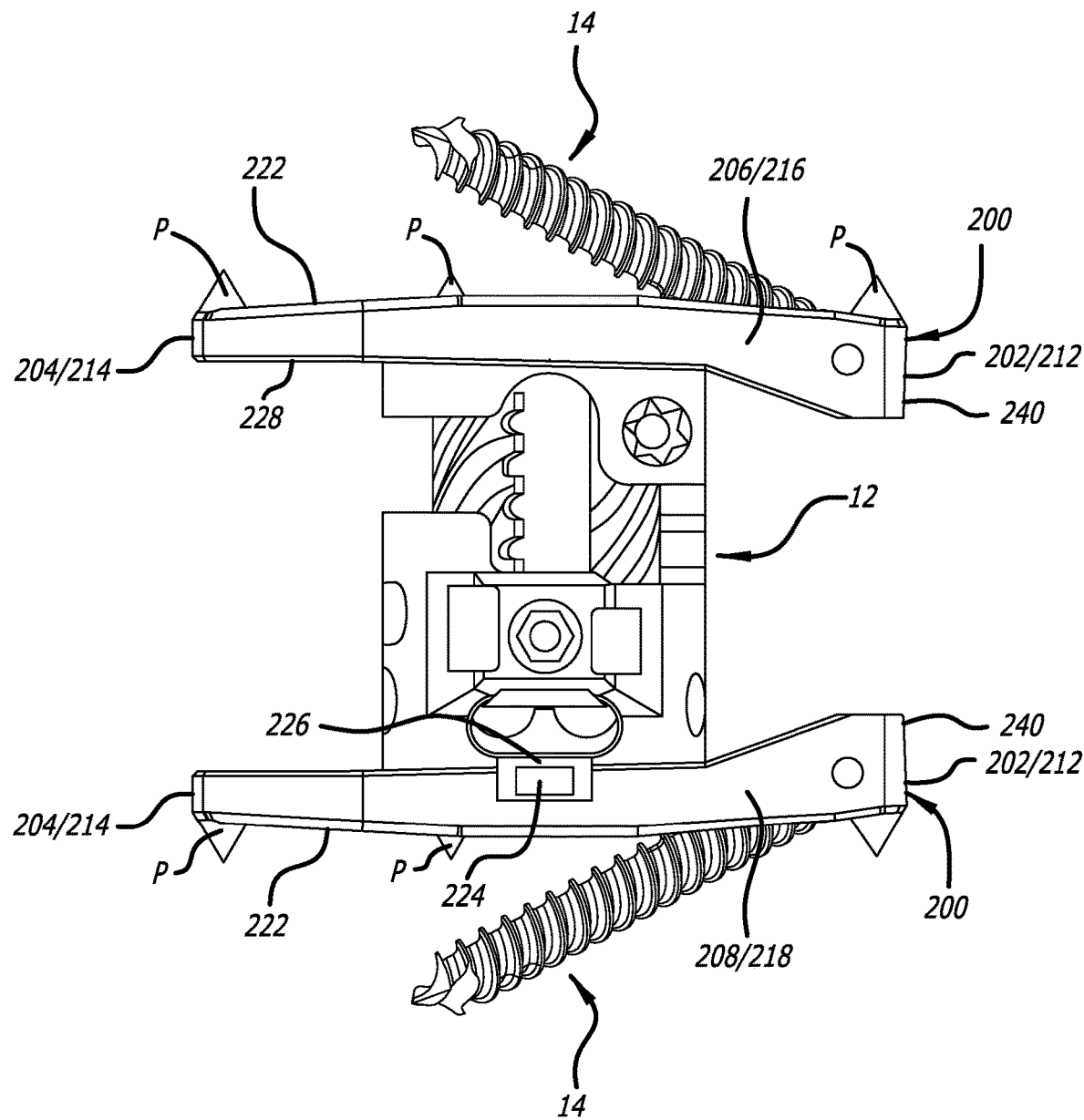
FIG. 9 is a side elevational view of a third embodiment of an end cap of the present disclosure including a first one of the end caps attached to a top portion of the spinal implant of FIG. 4, a second one of the end caps attached to a bottom portion of the spinal implant of FIG. 4, and first and second ones of the bone screws of the present disclosure inserted through the first one and the second one of the end caps, respectively.

Additional embodiments of the end cap of the present disclosure are generally indicated by the numeral' 100 in FIGS. 5-8 and by the numeral 200 in FIGS. 9-11. Like the end caps, one or more of the end caps 100 and/or one or more of the end caps 200 can be attached to the spinal implant 12 to, for example, increase the height, angularity, stability and anti-migration strength of the resulting combination. The end caps 100 and 200 can include many of the features of the end cap 10. For example, each of the end caps 100 and 200 can include interior cavities similar to the interior cavity 52 that afford attachment of a first one of the end caps 100 and 200 to the first flange portion 20 of the spinal implant 12, and attachment of a second one of the end caps 100 and 200 to the second flange portion 20 of the spinal implant 12. As depicted in FIGS. 5-8, the end cap 100 includes a first end 102, a second end 104, a first side 106, a second side 108, and a mid-longitudinal axis 110 extending through the first end 102 and the second end 104. Furthermore, as depicted in FIGS. 5-8, the end cap 100 can include first endwall 112 at and adjacent the first end 102, a second endwall 114 at and adjacent the second end 114, a first sidewall 116 adjacent the first side 106, a second sidewall 118 adjacent the second side 108, and a body portion 120 extending between the first endwall 112, the second endwall 114, the first sidewall 116, and the second sidewall 118.

The end cap 100 includes an exterior surface 122 formed on the body portion 120 formed between the first end 102, the second end 104, the first side 106, and the second side 108. The exterior surface 122 can be angled and/or shaped to conform or substantially conform to the endplate of a vertebral body, and/or can include one or more projections P formed thereon for penetrating into the endplate. As such, when engaged to the endplate of the vertebral body, the angle and/or shape of the exterior surface 122 and the projections P serve as the anti-migration features inhibiting movement of the end cap 100 (and the spinal implant 10 attached thereto) relative to the vertebral body.

Figure 6:
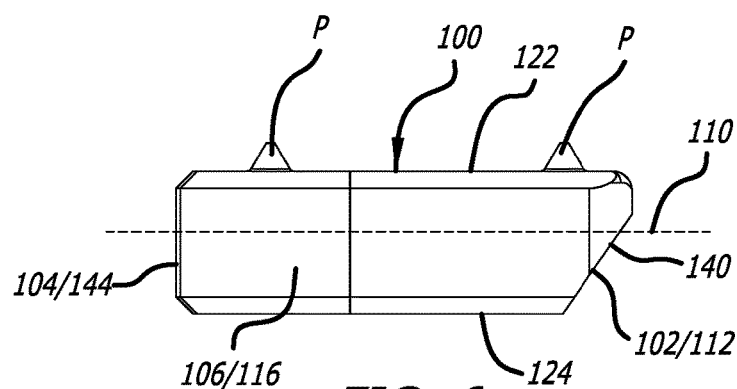
FIG. 6 is a side elevational view of the end cap of FIG. 5.

An interior cavity of the end cap 100 can be formed opposite from the exterior surface 122, and can be similar in configuration and function to the interior cavity 52 of the end cap 10. Like the interior cavity 52, the interior cavity of the end cap 100 can include a lip portion similar to the lip portion 60, as well as a flexible detent portion and a nub similar to the flexible detent portion 62 and the nub 64 that are used to facilitate attachment of either of the first flange portion 20 and the second flange portion 22 to end cap 100. In addition to the interior cavity, the end cap 100 can include a rim surface 124 formed on the first endwall 112, the second endwall 114, the first sidewall 116, and the second sidewall 118 adjacent the interior cavity and/or around the perimeter thereof, and at least a portion of the exterior surface 122 resides in a third plane and at least a portion of the rim surface 124 resides in a fourth plane, where the third plane and the fourth plane can be angled with respect to one another to be parallel, substantially parallel, and/or to provide a desired lordotic or kyphotic angle. As depicted in FIGS. 6 and 7, the exterior surface 122 and the rim surface 124 are angled so that the third plane and the fourth plane are parallel to one another. The exterior surface 122 could also be convex in planes aligned with or transverse to the mid-longitudinal axis 110.

An aperture 130 with a sidewall 132, as depicted in FIGS. 7 and 8, can be provided in the end cap 100 between the exterior surface 122 and an interior surface formed in the interior cavity opposite from the exterior surface 122. The aperture 130 can afford access to the spinal implant 12, and/or to afford bone growth from the endplate of the vertebral body therethrough and into the spinal implant 12. Additionally, the end cap 100 can include an end surface 140 formed on at least one of the first endwall 112, the second endwall 114, the first sidewall 116, and/or the second sidewall 118 that can be angled at an acute angle with respect to the exterior surface 122. As depicted in FIG. 7, the end surface 140 is formed on the first endwall 112. Bone screw holes 142 can be formed through the end cap 100, and extend from first openings 144 formed in the first endwall 112, the second endwall 114, the first sidewall 116, and/or the second sidewall 118 to second openings 146 formed in the exterior surface 122 and/or the sidewall 132. The end surface 140 can accommodate engagement of the threaded bone screws 14 received in the bone screw holes 142.

As depicted in FIGS. 9-11, the end cap 200 includes a first end 202, a second end 204, a first side 206, a second side 208, and a mid-longitudinal axis 210 extending through the first end 202 and the second end 204. Furthermore, as depicted in FIGS. 9-11, the end cap 200 can include first endwall 212 at and adjacent the first end 202, a second endwall 214 at and adjacent the second end 204, a first sidewall 216 adjacent the first side 206, a second sidewall 218 adjacent the second side 208, and a body portion 220 extending between the first endwall 212, the second endwall 214, the first sidewall 216, and the second sidewall 218.

The end cap 200 includes an exterior surface 222 formed on the body portion 220 formed between the first end 202, the second end 204, the first side 206, and the second side 208. The exterior surface 222 can be angled and/or shaped to conform or substantially conform to the endplate of a vertebral body, and/or can include one or more projections P formed thereon for penetrating into the endplate. As such, when engaged to the endplate of the vertebral body, the angle and/or shape of the exterior surface 222 and the projections P serve as the anti-migration features inhibiting movement of the end cap 200 (and the spinal implant 10 attached thereto) relative to the vertebral body.

An interior cavity of the end cap 200 can be formed opposite from the exterior surface 222, and can be similar in configuration and function to the interior cavity 52 of the end cap 10. Like the interior cavity 52, the interior cavity of the end cap 200 can include a lip portion similar to the lip portion 60, as well as a flexible detent portion 224 and a nub 226 (FIG. 9) similar to the flexible detent portion 62 and the nub 64 that are used to facilitate attachment of either of the first flange portion 20 and the second flange portion 22 to end cap 200. In addition to the interior cavity, the end cap 200 can include a rim surface 228 formed on the first endwall 212, the second endwall 214, the first sidewall 216, and the second sidewall 218 adjacent the interior cavity and/or around the perimeter thereof, and at least a portion of the exterior surface 222 can reside in a fifth plane and at least a portion of the rim surface 228 can reside in a sixth plane, where the fifth plane and the sixth plane can be angled with respect to one another to be parallel, substantially parallel, and/or to provide a desired lordotic or kyphotic angle. As depicted in 9, a first portion of the exterior surface 222 adjacent the first end 202 is angled at a first acute angle relative to central portions of the rim surface 228, a second portion of the exterior surface 222 adjacent the second end 204 is angled at a second acute angle relative to the central portions of the rim surface 228, and a third portion of the exterior surface 222 between the first portion and the second portion thereof is angled to be parallel to the central portions of the rim surface. As such, the exterior surface 222 is generally convex in planes aligned with the mid-longitudinal axis 210. The exterior surface 222 could also be convex in planes transverse to the mid-longitudinal axis 210.

An aperture 230 with a sidewall 232, as depicted in FIG. 11, can be provided in the end cap 200 between the exterior surface 222 and an interior surface formed in the interior cavity opposite from the exterior surface 222. The aperture 230 can afford access to the spinal implant 12, and/or to afford bone growth from the endplate of the vertebral body therethrough and into the spinal implant 12. Additional apertures 234 for access to the spinal implant 12, and/or to afford bone ingrowth can be provided on either side of the aperture 230. Additionally, the end cap 200 can include an end surface 240 formed on at least one of the first endwall 212, the second endwall 214, the first sidewall 216, and/or the second sidewall 218 that can be angled at a perpendicular or a substantially perpendicular angle with respect to the exterior surface 222. As depicted in FIG. 10, the end surface 240 is formed on the first endwall 212. Bone screw holes 242 can be formed through the end cap 200, and extend from first openings 244 formed in the first endwall 212, the second endwall 214, the first sidewall 216, and/or the second sidewall 218 to second openings 246 formed in the exterior surface 222 and/or the sidewall 232. The end surface 240 can accommodate engagement of the threaded bone screws 14 received in the bone screw holes 242.

Whereas, as depicted in FIG. 8, the maximum dimensions of the end cap 100 between the first end 102 and a second end 104, and between the first side 106' and a second side 108 are substantially equal, the corresponding maximum dimensions of the end cap 200, as depicted in FIG. 11, can be substantially different. The end cap 200 is configured to a have a greater maximum dimension between the first end 202 and the second end 204 than between a first side 206 and second side 208. As depicted in FIG. 11, the maximum dimension between the first end 202 and the second end 204 is approximately double the maximum dimension between the first side 206 and the second side 208. As such, the greater dimensions between the first end 102 and the second end 104 can allow the end cap 200 to span significant portions of, for example, the anterior-to-posterior dimension or the lateral-to-lateral dimension of the endplate.

Figure 12:
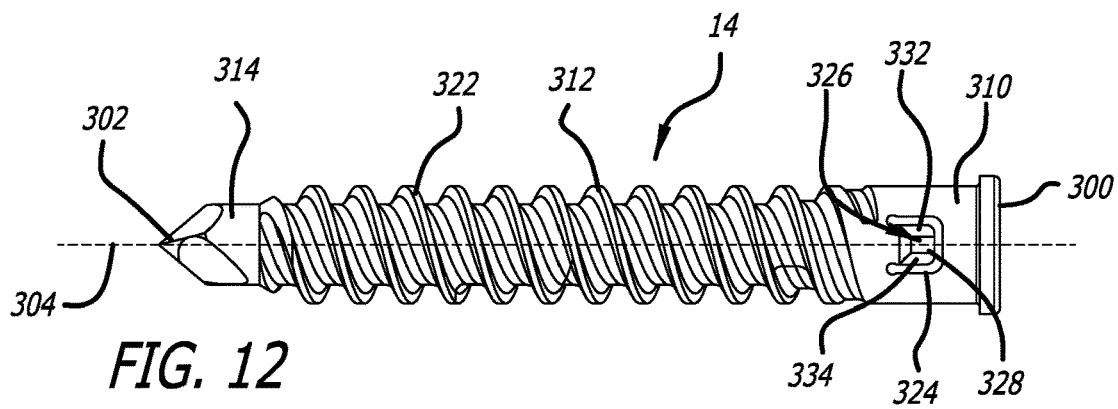
FIG. 12 is a side elevational view of the bone screw of the present disclosure.
Figure 13:
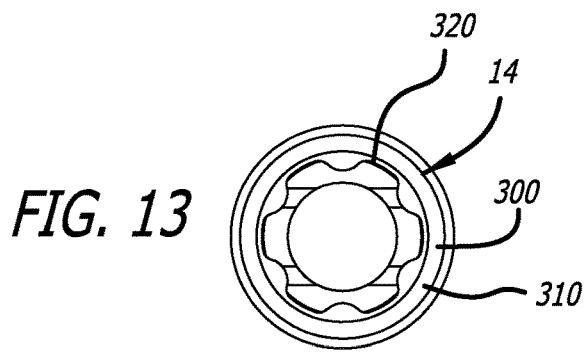
FIG. 13 is an enlarged end elevational view of the bone screw of the present disclosure.
Figure 14:
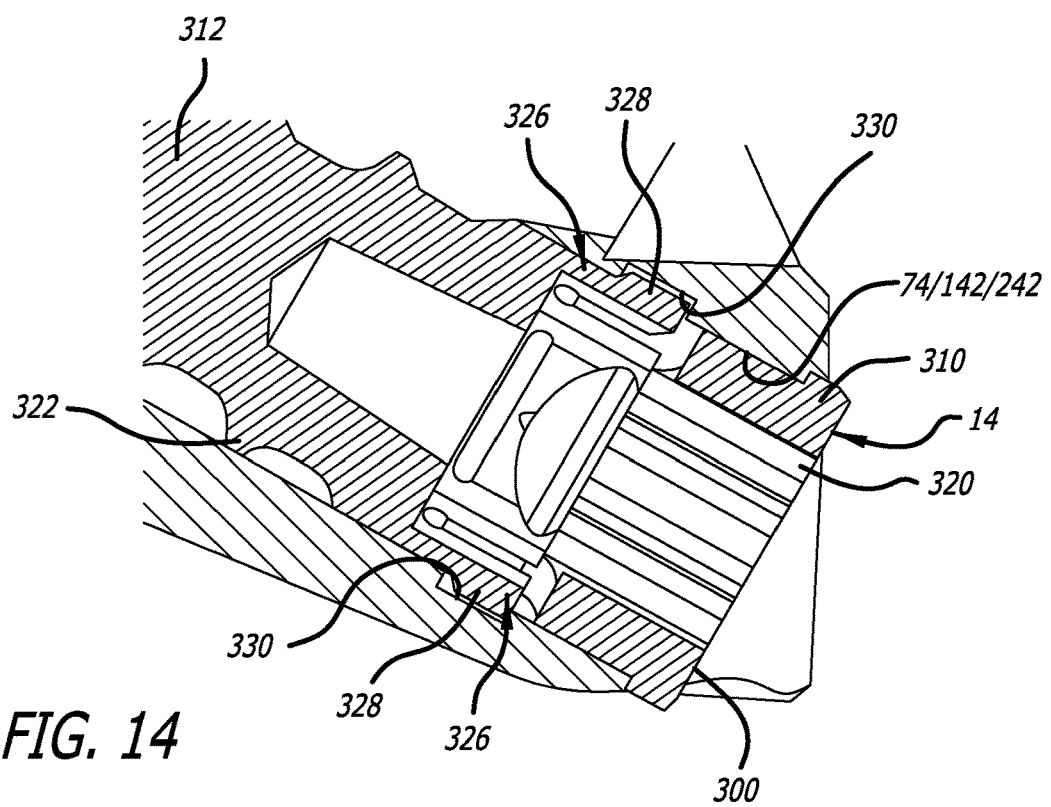
FIG. 14. is an enlarged cross-sectional view of the bone screw of the present disclosure positioned within a bone screw receiving hole formed in the end cap of FIG. 5.

The threaded bone screw 14 is also depicted in FIGS. 12-14. As depicted in FIG. 12, the threaded bone screw 14 used with the end caps 10, 10', and 10" can include a proximal end 300, a distal end 302, and an axis of rotation 304 extending through the proximal end 300 and the distal end 302. Furthermore, the threaded bone screw 14 can include a head portion 310, a shaft portion 312, and a tip portion 314. The head portion 310 can extend from the proximal end 300 to the shaft portion 312, the shaft portion 312 can extend from the head portion 310 to the tip portion 314, and the tip portion 314 can extend from the shaft portion 312 to the distal end 302.

The head portion 310 can include a tool-engaging recess 320 (FIG. 13) provided at the proximal end 300, the shaft portion 312 can include threads 322 (FIG. 12) for retention in the endplates of the vertebral bodies, and the tip portion 314 can be configured for self-drilling through the endplates of the vertebral bodies. Additionally, as depicted in FIGS. 12 and 14, the head portion 300 can include one or more aperture(s) 324 and corresponding spring tab portion(s) 326 extending from the head portion 310 and/or the shaft portion 312 into the aperture(s) 326. The spring tab portion(s) 326 can be biased in a first position, but can be flexible inwardly with respect to the corresponding aperture(s) 326. Each of the spring tab portion(s) 326 can include a nub 328 formed thereon.

The flexibility of the spring tab portion(s) 326 affords inward deflection thereof to allow insertion of the head portion 310 through portions of the bone screw holes 74, 142, and 242. Each of the bone screw holes 74, 142, and 242 can include recess(es) 330 (FIG. 14) for receiving the nub(s) 128 therein. As such, the head portion 310 can be inserted until bias of the spring tab portion(s) 326 to the first position forces the nub(s) 328 into the recess(es) 330. Receipt of the nub(s) 328 into the recess(es) 330 inhibits further insertion of the threaded bone screw 14 into the bone screw holes 74, 142, and 242, and also inhibits removal of the thread bone screw 14 from the bone screw receiving holes 74, 142, and 242. The nub(s) 328 can include inclined surfaces 332 and 334 that can aid deflection of the spring tab portion(s) 326 to facilitate entry of the spring tab portion(s) 326 into the recess(es) 330 during insertion of the threaded bone screw 14, and exiting of the spring tab portion(s) 326 out the recess(es) 330 during removal of the threaded bone screw 14.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. An end cap for use with a spinal implant used to replace portions of a vertebral body after a corpectomy thereof, the end cap comprising:
   a first end and a second end opposite from one another, a first side and a second side opposite from one another, and a mid-longitudinal axis extending through the first end and the second end;
   a body portion extending between the first end, the second end, the first side, and the second side, the body portion including a plurality of sidewalls defining a perimeter of the body portion and having lower edges and upper edges, rim surfaces provided on or adjacent the lower edges of the plurality of sidewalls and being oriented in a first direction, and an exterior surface extending between the upper edges of the plurality of sidewalls and being oriented in a second direction substantially opposite to the first direction, the exterior surface being configured to contact an end plate of a vertebral body; and
   an interior cavity formed in the end cap opposite from the exterior surface, the interior cavity being defined by an interior surface of the body portion and various side surfaces defining a perimeter of the interior cavity and terminating at the rim surfaces of the lower edges of the plurality of sidewalls;
   wherein the interior cavity is sized to receive a flange portion of the spinal implant, and includes a first attachment structure provided in the interior cavity facilitating non-pivotal attachment of the flange portion to the end cap, the receipt of the flange portion in the interior cavity and the non-pivotal attachment of the flange portion to the end cap allowing the flange portion to be securely nested within the interior cavity; and
   wherein one of the plurality of sidewalls, a corresponding one of the rim surfaces, and a corresponding one of the various side surfaces of the interior cavity are interrupted by gaps adjacent to and on either side of the first attachment structure on only one of the first end, the second end, the first side, and the second side, each of the gaps being uninterrupted by the one of the plurality of sidewalls adjacent the first attachment structure to afford deflection of the first attachment structure.

2. The end cap of claim 1, wherein the first end and the second end are spaced apart from one another a first maximum distance along the mid-longitudinal axis, and the first side and the second end are spaced apart from one another a second maximum distance in a direction perpendicular to the mid-longitudinal axis, the first maximum distance and the second maximum distance being substantially equal to one another.

3. The end cap of claim 1, wherein the first end and the second end are spaced apart from one another a first maximum distance along the mid-longitudinal axis, and the first side and the second end are spaced apart from one another a second maximum distance in a direction perpendicular to the mid-longitudinal axis, the first maximum distance being larger than the second maximum distance.

4. The end cap of claim 3, wherein the first maximum distance is approximately twice as large as the second maximum distance.

5. The end cap of claim 1, further comprising a second attachment structure including a lip portion projecting into the interior cavity adjacent a first side of the interior cavity, and wherein the first attachment structure is a detent portion including a nub provided adjacent a second side of the interior cavity, a first portion of the flange portion being receivable between the lip portion and the interior surface of the body portion, and a second portion of the flange portion being receivable between the nub and the interior surface of the body portion.

6. The end cap of claim 5, wherein the detent portion is flexible to afford passage of the second portion of the flange portion past the nub to afford capture of the flange portion in the interior cavity and corresponding attachment of the end cap to the flange portion.

7. The end cap of claim 1, wherein the rim surface surrounds at least portions of the interior cavity, and wherein at least portions of the exterior surface reside in a first plane, and at least portions of the rim surface reside in a second plane, the first plane and the second plane being one of parallel to one another, substantially parallel to one another, and oriented at an acute angle to one another.

8. The end cap of claim 7, wherein portions of the exterior surface is convex in planes at least one of aligned with the mid-longitudinal axis and transverse to the mid-longitudinal axis.

9. The end cap of claim 7, wherein the exterior surface has multiple planar surfaces angled with respect to one another.

10. The end cap of claim 1 in combination with a threaded bone screw, wherein the end cap includes a bone screw hole formed therein for receiving the threaded bone screw, and the bone screw hole includes a recess formed therein; and wherein the threaded bone screw includes a head portion with an aperture formed therein and a spring tab portion extending into the aperture, the spring tab portion being biased in a first position and being flexible inwardly relative to the aperture, and the head portion being insertable through the bone screw hole until bias of the spring tab portion forces a nub formed thereon into the recess.

11. The combination of claim 10, wherein receipt of the nub in the recess inhibits further insertion and removal of the threaded bone screw relative to the bone screw hole.

12. An end cap for use with a spinal implant used to replace portions of a vertebral body after a corpectomy thereof, the end cap comprising:
   a first end and a second end opposite from one another, a first side and a second side opposite from one another, and a mid-longitudinal axis extending through the first end and the second end;
   a body portion extending between the first end, the second end, the first side, and the second side, the body portion including a plurality of sidewalls defining a perimeter of the body portion and having lower edges and upper edges, rim surfaces provided on or adjacent the lower edges of the plurality of sidewalls and being oriented in a first direction, and an exterior surface extending between the upper edges of the plurality of sidewalls and being oriented in a second direction substantially opposite to the first direction, the exterior surface being configured to contact an end plate of a vertebral body; and an interior cavity formed in the end cap opposite from the exterior surface, the interior cavity being defined by an interior surface of the body portion and various side surfaces defining a perimeter of the interior cavity and terminating at the rim surfaces of the lower edges of the plurality of sidewalls; and wherein the interior cavity is sized to receive a flange portion of the spinal implant, and includes a first attachment structure provided in the interior cavity facilitating non-pivotal attachment of the flange portion to the end cap, the receipt of the flange portion in the interior cavity and the non-pivotal attachment of the flange portion to the end cap allowing the flange portion to be securely nested within the interior cavity; and wherein one of plurality of sidewalls, a corresponding one of the rim surfaces, and a corresponding one of the various side surfaces of the interior cavity are interrupted by gaps adjacent to and on either side of the first attachment structure on only one of the first end, the second end, the first side, and the second side, each of the gaps being uninterrupted by the one of the plurality of sidewalls adjacent the first attachment structure to afford deflection of the first attachment structure;

wherein at least portions of the exterior surface reside in a first plane, and at least portions of the rim surfaces reside in a second plane, the first plane and the second plane being one of parallel to one another, substantially parallel to one another, and oriented at an acute angle to one another.

13. The end cap of claim 12, wherein the first end and the second end are spaced apart from one another a first maximum distance along the mid-longitudinal axis, and the first side and the second end are spaced apart from one another a second maximum distance in a direction perpendicular to the mid-longitudinal axis, the first maximum distance and the second maximum distance being substantially equal to one another.

14. The end cap of claim 12, wherein the first end and the second end are spaced apart from one another a first maximum distance along the mid-longitudinal axis, and the first side and the second end are spaced apart from one another a second maximum distance in a direction perpendicular to the mid-longitudinal axis, the first maximum distance being larger than the second maximum distance.

15. The end cap of claim 14, wherein the first maximum distance is approximately twice as large as the second maximum distance.

16. The end cap of claim 12, further comprising a second attachment structure including a lip portion projecting into the interior cavity adjacent a first side of the interior cavity, and wherein the first attachment structure is a detent portion including a nub provided adjacent a second side of the interior cavity, a first portion of the flange portion being receivable between the lip portion and the interior surface of the body portion, and a second portion of the flange portion being receivable between the nub and the interior surface of the body portion.

17. The end cap of claim 16, wherein the detent portion is flexible to afford passage of the second portion of the flange portion past the nub to afford capture of the flange portion in the interior cavity and corresponding attachment of the end cap to the flange portion.

18. The end cap of claim 12, wherein portions of the exterior surface are convex in planes at least one of aligned with the mid-longitudinal axis and transverse to the mid-longitudinal axis.

19. The end cap of claim 12 in combination with a threaded bone screw, wherein the end cap includes a bone screw hole formed therein for receiving the threaded bone screw, and the bone screw hole includes a recess formed therein; wherein the threaded bone screw includes a head portion with an aperture formed therein and a spring tab portion extending into the aperture, the spring tab portion being biased in a first position and being flexible inwardly relative to the aperture, and the head portion being insertable through the bone screw hole until bias of the spring tab portion forces a nub formed thereon into the recess; and wherein receipt of the nub in the recess inhibits further insertion and removal of the threaded bone screw relative to the bone screw hole.

20. An end cap for use with a spinal implant used to replace portions of a vertebral body after a corpectomy thereof, the end cap comprising:

a first end and a second end opposite from one another, a first side and a second side opposite from one another, and a mid-longitudinal axis extending through the first end and the second end;

a body portion extending between the first end, the second end, the first side, and the second side, the body portion including a plurality of sidewalls provided at the first end, the second end, the first side, and the second side, lower edges and upper edges provided on the plurality of sidewalls, rim surfaces provided on or adjacent the lower edges of the plurality of sidewalls and being oriented in a first direction, and an exterior surface extending between the upper edges of the plurality of sidewalls and being oriented in a second direction substantially opposite to the first direction; and an interior cavity formed in the end cap opposite from the exterior surface, the interior cavity being defined by an interior surface of the body portion and various side surfaces defining a perimeter of the interior cavity; and wherein the interior cavity is sized to receive a flange portion of the spinal implant, and includes a first attachment structure provided in the interior cavity facilitating non-pivotal attachment of the flange portion to the end cap, the receipt of the flange portion in the interior cavity and the non-pivotal attachment of the flange portion to the end cap allowing the flange portion to be securely nested within the interior cavity; and wherein one of the plurality of sidewalls, a corresponding one of the rim surfaces, and a corresponding one of the various side surfaces of the interior cavity are interrupted by gaps adjacent to and on either side of the first attachment structure on only one of the first end, the second end, the first side, and the second side, each of the gaps being uninterrupted by the one of the plurality of sidewalls adjacent the first attachment structure to afford deflection of the first attachment structure;

wherein at least portions of the exterior surface reside in a first plane, and at least portions of the rim surfaces reside in a second plane, the first plane and the second plane being one of parallel to one another, substantially parallel to one another, and oriented at an acute angle to one another.

\* \* \* \* \*